United States Patent

Kooi et al.

Patent Number: 5,953,117
Date of Patent: Sep. 14, 1999

[54] VISUAL PROMINENCE METER

[75] Inventors: Frank Leonard Kooi, Utrecht; Alexander Hans Wertheim, Maarsbergen; Kees Moddemeijer, Leiden, all of Netherlands

[73] Assignee: Nederlandse Organisatie voor Toegepast-Natuurwetenschappelijk Onderzoek (TNO), Delft, Netherlands

[21] Appl. No.: 09/068,159

[22] PCT Filed: Nov. 1, 1996

[86] PCT No.: PCT/NL96/00431

§ 371 Date: Jun. 4, 1998

§ 102(e) Date: Jun. 4, 1998

[87] PCT Pub. No.: WO97/16112

PCT Pub. Date: May 9, 1997

[30] Foreign Application Priority Data

Nov. 3, 1995 [NL] Netherlands ............. 1001571

[51] Int. Cl.⁶ .................................... A61B 3/024
[52] U.S. Cl. ............................................. 356/256
[58] Field of Search ............. 356/256; 351/224, 351/225, 239

[56] References Cited

U.S. PATENT DOCUMENTS

| 1,854,724 | 4/1932 | Tillyer | 351/225 |
| 5,024,519 | 6/1991 | Howard et al. | 351/226 |
| 5,061,060 | 10/1991 | Aulhorn et al. | 351/224 |
| 5,202,711 | 4/1993 | Klingbeil | 351/224 |

FOREIGN PATENT DOCUMENTS

| 0 307 604 | 3/1989 | European Pat. Off. |
| 39 22 471 | 1/1991 | Germany . |
| WO 95/08290 | 3/1995 | WIPO . |

*Primary Examiner*—Richard A. Rosenberger
*Attorney, Agent, or Firm*—Young & Thompson

[57] ABSTRACT

Method for a visual measurement, in which an image sector of an image with a target object is presented to an eye of an operative by a display unit, and in which the fovea of the eye is placed into such a reference position relative to the display unit, or the image sector is shifted in such a way towards the periphery relative to the fovea of the eye in a reference position, that the target object lies outside the fovea and the operative decides whether the target object is still visible, and the extent to which the target object is situated outside the reference position is determined.

12 Claims, 2 Drawing Sheets

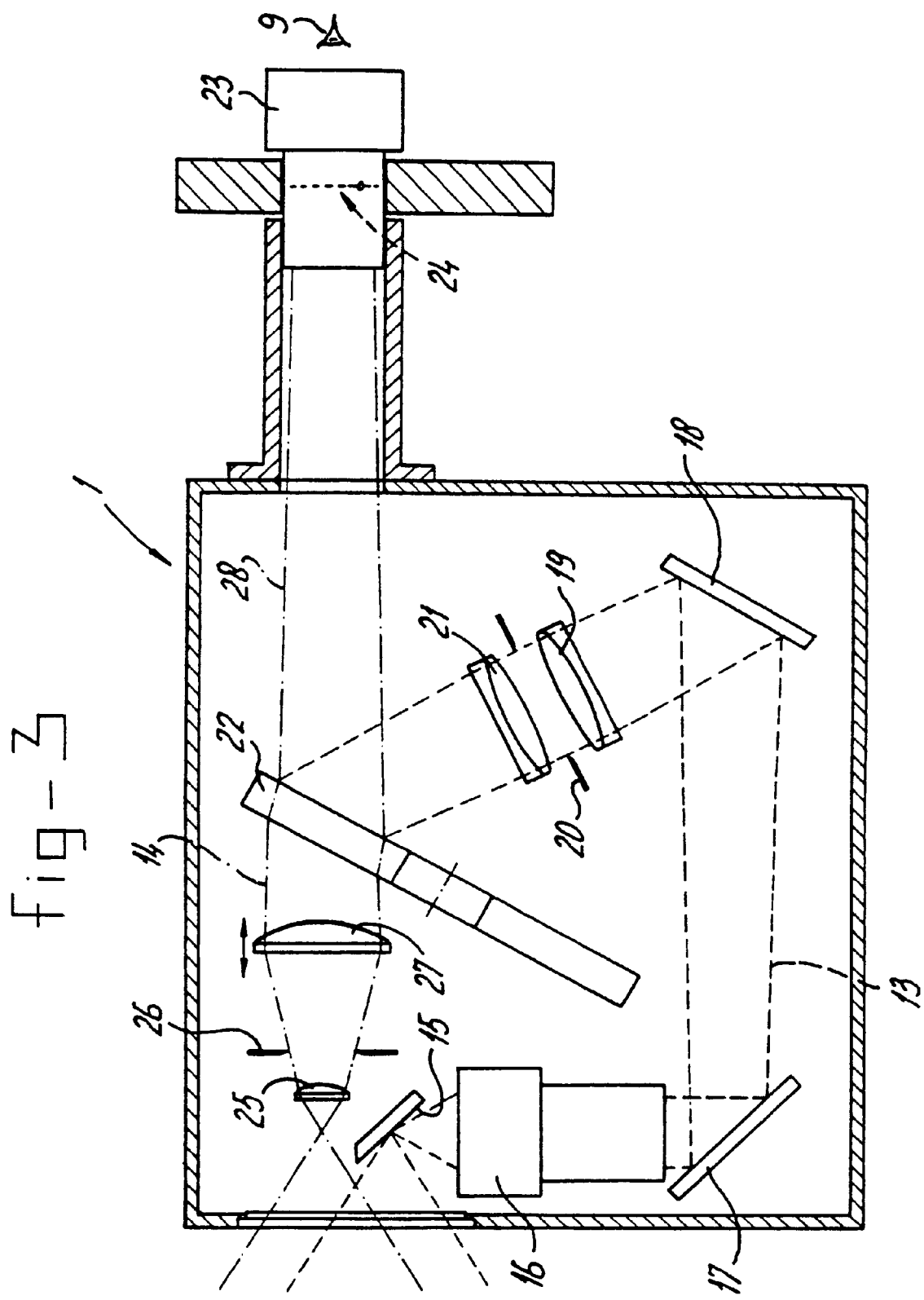

VISUAL PROMINENCE METER

BACKGROUND OF THE INVENTION

The invention relates to both a visual measuring method and a visual measuring device, in particular for determining the visual prominence of a target object within an image. The invention can be carried out both with purely optical techniques and with all kinds of combinations of optoelectronic techniques. The invention is explained below in particular, but not restrictively, with reference to exemplary embodiments on the basis of purely optical techniques.

SUMMARY OF THE INVENTION

There has long been a desire to determine as objectively as possible the visual prominence of a target object, for example a traffic sign, within an image, for example a street scene. The object of the invention is to provide both a method and a device by means of which that desire can be fulfilled.

On the one hand, the invention is based on the realization that the objective measure used for visual prominence can be the extent to which a target object situated in an image is moved towards the periphery of the field of vision of an eye while the operative is still just capable of perceiving the target object in the periphery of his field of vision. On the other hand, the invention is based on the idea that the reliability of the objective measurements increases when the image, with the target object therein in each case, is presented for a relatively short time to the operative. It is expected that disturbing subjective value judgments will be filtered out as well as possible in this way. The invention is also based on the idea that the extent of a contrast reduction in the image sector presented to the eye can be a secondary measure of determining the visual prominence of a target object within an image.

BRIEF DESCRIPTION OF THE DRAWINGS

The invention is explained in greater detail below on the basis of non-restrictive exemplary embodiments with reference to the drawings, in which:

FIG. 3 shows a diagrammatic view of a third variant of an embodiment of the measuring device according to the present invention, including an illustration of its housing, and showing only the main parts.

DESCRIPTION OF THE PREFERRED EMBODIMENTS

Figure 1:
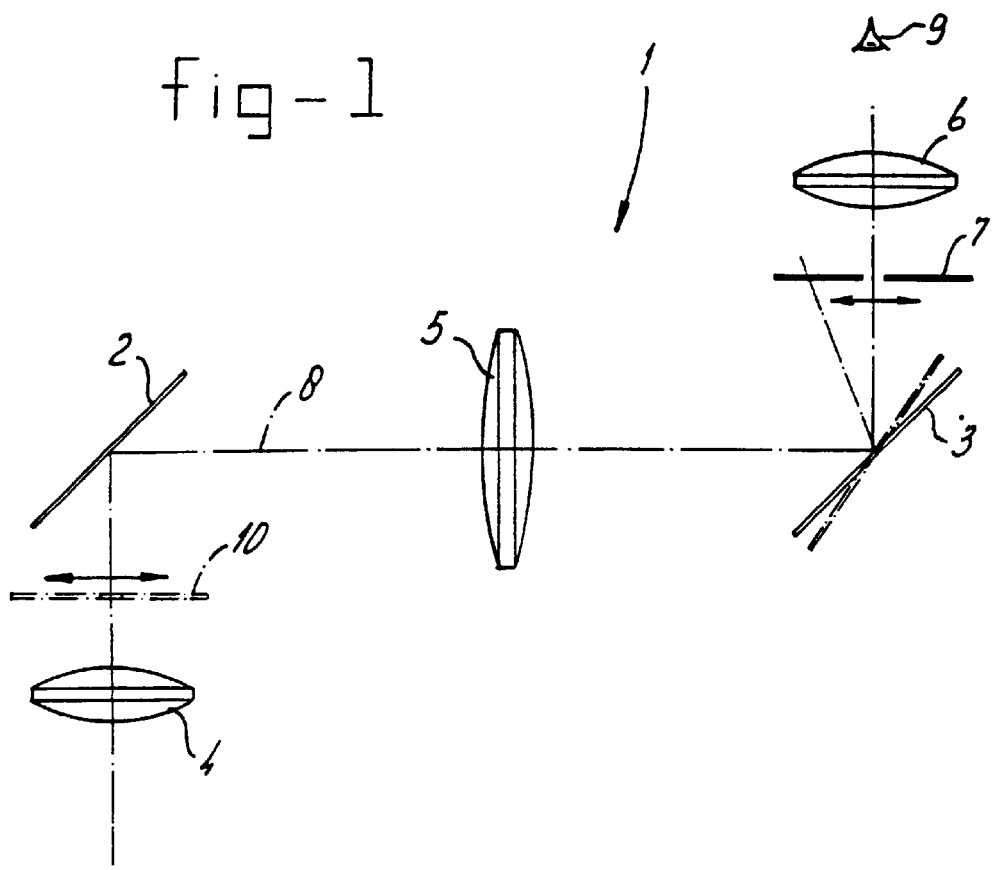
FIG. 1 shows diagrammatically an optical measuring device according to a first embodiment of the invention, in which only the main parts are shown.

The measuring device 1 shown in FIG. 1 comprises essentially two mirrors 2, 3 and three lenses 4, 5 and 6. A diaphragm 7 with an adjustable diaphragm aperture is also present. The light path from the image (not shown) to the eye 9 is indicated diagrammatically by the dashed-and-dotted line 8. An image can be viewed with the eye 9 in a fixed position, for example assisted in this by an eye fixation point which is accommodated in, for example, the image plane of the lens 6. By means of the tilting mirror 3, the image can be viewed at two different angles, so that the target object is projected at two different points onto the retina of the eye 9. With the diaphragm 7 it is also possible to present the whole image to the eye 9 (diaphragm 7 opened fully), or to present just a detail of that image (diaphragm 7 opened only slightly). It is now ensured that with the eye 9 in the reference position the detail in the image, with essentially only the target object, is projected onto or essentially onto the fovea of the retina, so that the detail of the image is situated in a "center forward" position in front of the eye 9. If the mirror 3 is now tilted through a predetermined angle and the diaphragm 7 is opened fully at the same time, the full image is presented to the eye 9, but with the target object shifted towards the periphery of the field of vision of the eye 9. The operative now decides whether in that situation, with his eye 9 still directed at the reference point, he can or cannot perceive the target object in the periphery of his field of vision. The angle through which the mirror 3 is tilted is adjusted, following which the image detail and the full image are again presented alternately in succession. The angle through which the mirror 3 is tilted so that the operative can perceive or just fails to be able to perceive the target object in the periphery of his field of vision can be used as a measure of the visual prominence of that target object within the image in question. By way of example, a variant is also shown in FIG. 1, where a diaphragm 10 shown in an imaginary way replaces the diaphragm 7. Other variants are also conceivable, for example in which the mirror 2 can be tilted. Instead of making the mirror 3 tilt relatively quickly between its two end positions, in which case the aperture in the diaphragm 7 is preferably adjusted simultaneously, the following variant is also conceivable, based on a slightly adapted measuring method: any diaphragm is now dispensed with, or is placed in such a position that a large part of the image, with the target object therein as one of the parts, is presented to the eye 9. The optical system is placed in such a position that the target object is situated initially in the center of the image. The target object is now gradually shifted towards the periphery of the field of perception by striving for a gradual adjustment in the optical system, for example by gradually tilting the mirror 3. The angular displacement of the mirror 3 at the moment when the operative, with his eye 9 directed at the reference point in the optical system, still just perceives or just fails to perceive the target object in the periphery of his field of vision is a measure of the visual prominence of that target object within that image.

When two image sectors are presented alternately in succession, it is preferable first to present an image sector in which the target object is projected onto the fovea of the eye directed at a fixation point, and then, by depressing, for example, an exposure lever to present the second image sector with the target object shifted towards the periphery immediately after the first image sector, and for a relatively short time in the range from ¹⁄₁₀ to 10 s, preferably ⅛ to 8 s.

Figure 2:
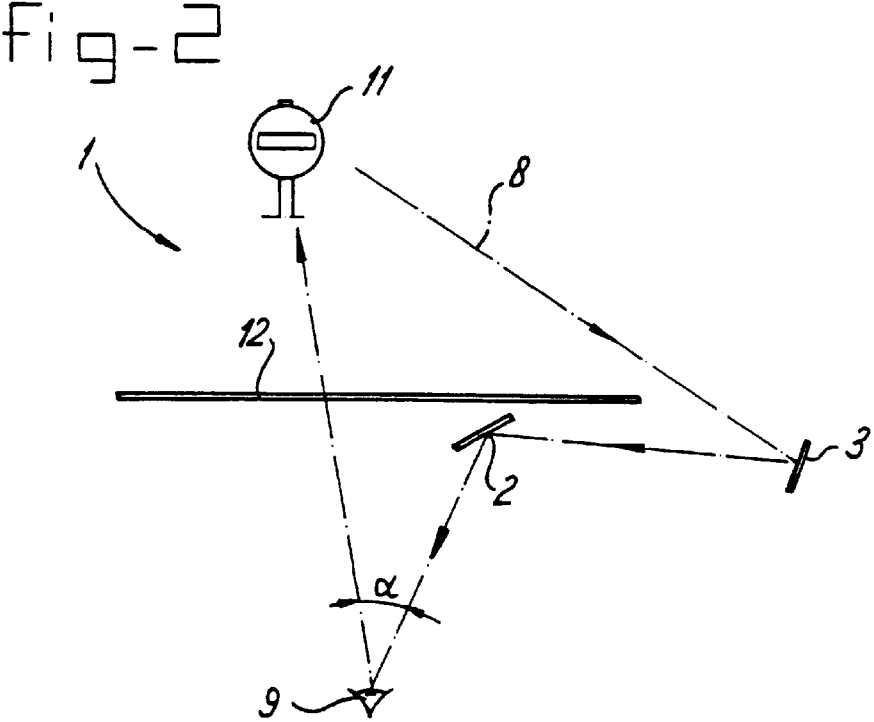
FIG. 2 shows a diagrammatic view of a second variant of an embodiment of an optical measuring device according to the invention, illustrating a target object, and in which only the main parts are shown.

FIG. 2 shows a further variant of the invention by means of which two images can be presented in relatively rapid succession. In this case the operative has before him an image in which there is, for example, a traffic sign as the target object 11. A screen 12 is situated between the image and the eye 9. When this screen 12 is actuated, the image in front of the eye 9 is covered. The screen 12 can be, for example, an LCD screen which can change relatively quickly between a matt, opaque and a bright, transparent appearance. There is also a system of two mirrors 2, 3, by means of which an image detail can be projected round the outside of the screen. The idea is that the image detail should comprise essentially only the target object 11, possibly with the immediate environment. The target object 11 projected by the mirrors 2 and 3 serves as the fixation point for the eye 9 of the operative. If the screen 12 is now switched on and off alternately, the complete scene with the target object 11 in the periphery of the field of vision is presented alternately to the eye 9. The target object 11 remains in the center of the field of vision, i.e. on the fovea, by means of mirrors 2 and 3. The angle α is taken here as the measure of visual prominence. A diaphragm, for example, could be considered as an alternative to the screen 12.

The advantage of such a device is that there is no distortion of the image presented through lenses and the like, and that a large aperture angle of the field of vision is obtained.

FIG. 3 shows yet a further variant of the device according to the invention. In the case of this device 1 the image of a scene reaches the eye 9 by way of two light paths 13, 14. For this purpose, the light path 13 defined by a mirror 15, an eyepiece 16, mirrors 17, 18, a first doublet lens 19, an adjustable diaphragm 20, a second doublet lens 21, a variable beam-splitting mirror 22 and, finally, an eyepiece 23. The eyepiece 23 contains an adjustable eye fixation feature 24. By way of the light path 14, the light reaches the eye 9 after passing in succession a fixed lens 25, a fixed diaphragm 26, a lens 27 which is movable in the lengthwise direction of the light path 14, the variable beam-splitting mirror 22 and the eyepiece 23. The elements situated along the light path 13 ensure that the scene, possibly enlarged or reduced, is projected in focus on the retina of the eye 9. On the other hand, the elements situated along the light path 14 ensure that the scene, possibly enlarged or reduced to the same extent as in the case of the light path 13, is projected in focus on the pupil of the eye 9, instead of on the retina. A so-called Maxwellian view is consequently achieved with the light path 14, which means that the retina of the eye 9 perceives the scene as a sort of mist.

In order to ensure that very conspicuous objects (for example, objects which are very close up) do not still remain easily visible when the greatest possible peripheral shift takes place—with the result that such objects cannot be measured—it is possible to add an image degradation combined with the peripheral shift, in such a way that the amount of light in the eye is not affected. For this purpose, contrast reduction of the entire image sector can be used, by means of a round semi-transparent mirror which reduces contrast in a linear manner running upwards from 0 to 100%, and which is placed in one of the two light paths in such a way (see FIG. 3, number 22) that—in combination with a lens right next to the eye (see FIG. 3, number 25)—a Maxwellian view occurs in that light path. The mirror can then be turned by hand into the desired contrast reduction position. Another setting method is mechanical connection of the contrast reduction setting device (i.e. the mirror) to the peripheral shift. Other contrast reduction methods are also possible, for example using a linear 0 to 100% transparent frosted glass, instead of the mirror. If such a frosted glass is connected mechanically to the peripheral shift, one light path alone will suffice, and a Maxwellian view is no longer necessary.

The two light paths 13, 14 can now be combined by means of the variable beam-splitting mirror 22. The position of that beam-splitting mirror 22 determines the ratio between the in-focus and the out-of-focus image on the eye 9, and thus the contrast of the target object within the scene. The exit pupil of the device 1 is adjustable for both light paths 13, 14. For the light being transmitted by way of the light path 13, this is achieved by means of an adjustable diaphragm 20. For the light being transmitted by way of the light path 14, this is achieved by means of the movable lens 27. The adjustment mechanism of the diaphragm 20 and the lens 27 respectively are connected, so that the pupil size is always the same for the two light paths 13, 14. This ensures that the exit pupil of the device is always smaller than the pupil of the eye 9. Depending on the light conditions, the pupil of the eye will be larger or smaller, so that the exit pupil of the device 1 must be adapted to it. The eye fixation feature 24 is a small black dot, to which the observer can direct the eye 9 during a measurement. Said eye fixation feature 24 is adjustable by means of a micrometer (not visible). For a measurement the procedure is as follows: the exit pupil of the device 1 is first adjusted depending on the light conditions. The device is then directed at the scene in such a way that the target object is centered relative to the eye fixation feature 24 on which the operative is keeping his eye 9 directed. The desired contrast can now be set using the variable beam-splitting mirror 22. If desired, the contrast setting may be carried out already before the apparatus 1 is directed at the scene. The operative can then direct his eye 9 at another part of the scene, while continuing to look through the apparatus 1, so that the target object is shifted towards the periphery of the field of vision of the eye 9. Such a shift can be achieved by either turning the device 1 in its entirety through an angle, or by adjusting the eye fixation feature 24. In both cases the extent to which the target object is moved to the periphery is measurable. The operative can now shift the target object towards the periphery of the field of vision of his eye 9 precisely so far that the target object is no longer perceptible with the eye 9, and this gives a measure of the visual prominence. Another possibility is to move the target object towards the periphery of the field of vision of the eye 9, and then to change the contrast of the target object within the scene, by adjusting the beam-splitting mirror 22, for example until the target object is no longer perceptible for the operative. The extent to which the target object is shifted towards the periphery of the field of vision of the eye 9 in combination with the contrast at which the target object is no longer visible for the operative can then be used as a measure of the visual prominence of the target object within the scene.

It will be clear to the person skilled in the art that the variant of an embodiment of the device 1 shown in FIG. 3 is essentially the same as that of FIG. 1 in the situation where the light path 14 is fully switched off. In this variant of an embodiment shown in FIG. 1 the target object can also be shifted towards the periphery of the field of vision of the eye 9 by turning the device 1 in its entirety, or by adjusting an eye fixation feature in, for example, the lens 6, instead of tilting the mirror 3.

The ideas for measuring the visual prominence by adjusting the contrast of the target object within a scene and the idea of presenting to the eye in succession within a short period of time a centered target object (projection onto the fovea) and shifting a scene with the target object towards the periphery can also be combined by, for example, combination of the embodiments shown in FIGS. 1 and 3. For example, the system of lenses, mirrors and diaphragms shown in FIG. 1 is set up in the device 1 of FIG. 3 in the part through which the light path 28 travels (the combination of the light paths 13 and 14 after the variable beam-splitting mirror 22).

A further variant with the working principle according to the device 1 of FIG. 3 could be as follows: the variable beam-splitting mirror 22 is replaced by a fixed beam-splitting mirror. Sets of a fixed and an adjustable polaroid filter are placed in both the light path 13 and the light path 14. The adjustable polaroid filters are connected, so that they are adjusted to the same extent. The sets of polaroid filters in the respective light paths 13, 14 are designed in such a way that on setting of the adjustable polaroid filters the light transmission is increased along one light path and reduced along the other light path, or vice versa, so that the contrast of the target object within the scene can be changed by changing the ratio between image on the pupil of the eye and on the retina of the eye 9. The sets of polaroid filters are formed from, for example, a fixed polaroid filter which is rotated through ninety degrees relative to the fixed polaroid filter in the other light path. The adjustable polaroid filters are also formed by a common polaroid filter which rotates about its center point and covers both the light path 13 and the light path 14.

We claim:

1. A method for determining the visual prominence of a target object in an image comprising the steps of:

presenting by a display unit an image sector of the image with the target object to an eye of an operative;

placing the fovea of the eye into a reference position relative to the display unit;

shifting the image sector towards the periphery relative to the fovea of the eye until the target becomes no longer visible; and measuring the extent of the shift from the reference position to the position where the target becomes no longer visible as a measure of the visual prominence of the target object.

2. Method according to claim 1, in which a second image sector of the same image is formed, in the case of which second image sector the target object is presented to the fovea, and the two image sectors are presented in succession in a relatively short time.

3. Method according to claim 2, in which the second image sector is configured in such a way so as to present essentially only the target object.

4. The method of claim 1, comprising the further step of using a display unit that is suitable for presenting different images to the eye.

5. The method of claim 1, comprising the further steps of using a display unit with a variable contrast display, and adjusting the contrast of the variable contrast display so that the contrast of the images is varied with respect to the image surroundings.

6. The method of claim 1, wherein the steps of presenting by a display unit an image sector of the image with the target object to an eye of an operative and placing the fovea of the eye into a reference position relative to the display unit, places the reference position within the image sector.

7. Visual measuring device for determining the visibility of a target object in an image, provided with a display unit for presenting an image sector of an image with a target object to an eye of an operative, having a reference point for directing the fovea of the eye into a reference position relative to the image sector, having adjusting means for changing the position of the area of the image to be presented with the image sector relative to the reference point, and having a measuring device for determining the extent to which the target object lies outside the reference point as a measure for the visibility of the target object, with the display unit equipped in such a way that two image sectors of the same image can be presented in succession in a relatively short time, with the target object in a mutually shifted position.

8. Device according to claim 7, in which the display unit comprises an optical system with a mirror element, which is moveable between two annular positions, for the purpose of influencing the light transmission with the optical system in such a way that two image sectors of the same image can be presented relatively shortly after one another, with the target object in a mutually shifted position, and connected to said element for influencing the light path an image sector defining element which can assume two different positions, in order to present two image sectors of different sizes.

9. The device of claim 8, wherein said image sector defining element comprises a diaphragm.

10. Device according to claim 7, in which the display unit comprises a display viewing surface with a controllable contrast designed to adjust the viewed contrast within the image sector.

11. Device according to claim 10, in which a light path dividing element is situated in or on the display unit, in order to split the light path into two partial light paths for presentation of the image sector, with a separate optical system for each partial light path, for presenting one partial light path in focus and the other partial light path out of focus, and with a light path combining element downstream of those separate optical systems, in order to combine the two partial light paths in an adjustable ratio and present them to the eye.

12. Visual measuring device for determining the visibility of a target object in an image, comprising a display unit for presenting a first image sector of an image with a target object to an eye of an operative, a reference point for directing the fovea of the eye into a reference position relative to the first image sector, adjusting means for changing the position of the area of the image to be present with a second image sector relative to the reference point, a measuring device for determining the extent to which the target object lies outside the reference point as a measure for the visibility of the target object, and a screen element which can assume a light-transmitting display position and a non-light-transmitting covering position, in which in the covering position the first image sector is covered and the second image sector is presented to the eye via a mirror, around the screen element.

* * * * *